United States Patent [19]
Byrd

[11] Patent Number: 5,276,932
[45] Date of Patent: Jan. 11, 1994

[54] MANUALLY OPERATED ROTARY TOOTHBRUSH

[76] Inventor: Ralph Byrd, 91D Harmony Hill Rd., Albany, N.Y. 12203

[21] Appl. No.: 882,613

[22] Filed: May 13, 1992

[51] Int. Cl.$^5$ .................................. A46B 13/08
[52] U.S. Cl. .............................. 15/28; 15/22.1; 74/89.17
[58] Field of Search ............ 15/25, 26, 28, 29, 22.1; 74/89, 89.17

[56] References Cited

U.S. PATENT DOCUMENTS

| | | | |
|---|---|---|---|
| 1,561,062 | 11/1925 | Douglas | 15/26 |
| 1,947,324 | 2/1934 | Zerbee | 15/28 |
| 1,949,241 | 2/1934 | Carlson et al. | 15/25 |
| 2,140,307 | 12/1938 | Belaschic et al. | 15/22.1 |
| 3,115,652 | 12/1963 | Zerbee | 15/28 |
| 4,048,690 | 9/1977 | Wolfson | 15/29 |
| 4,079,517 | 3/1978 | Zacharia | 32/59 |
| 4,274,173 | 6/1981 | Cohen | 15/28 |
| 5,068,939 | 12/1991 | Holland | 15/22.1 |

FOREIGN PATENT DOCUMENTS

| | | | |
|---|---|---|---|
| 807900 | 1/1937 | France | 15/28 |
| 292744 | 11/1953 | Switzerland | 15/26 |

*Primary Examiner*—Harvey C. Hornsby
*Assistant Examiner*—Gary K. Graham
*Attorney, Agent, or Firm*—Schmeiser, Morelle & Watts

[57] ABSTRACT

Improvements to a manually operated, rotary bristle toothbrush. A thumb actuated mechanism is slidably and longitudinally mounted in an essentially hollow, elongate handle and a part of the mechanism, a rack, is caused to engage at least one compound pinion/spur gear in order to convert longitudinally reciprocative motion to rotary motion that is shunted toward the head of the toothbrush. The head contains therein one or more rotary bristles that project orthogonally from the head of the toothbrush and off the major longitudinal axis of the device. Rotary motion is conducted by a drive shaft into the head of the brush and transferred via a crown gear to bases of the brush(es) by interface between the crown gear of the drive shaft and at least one brush base comprising a capstan device adapted for rotation.

7 Claims, 2 Drawing Sheets

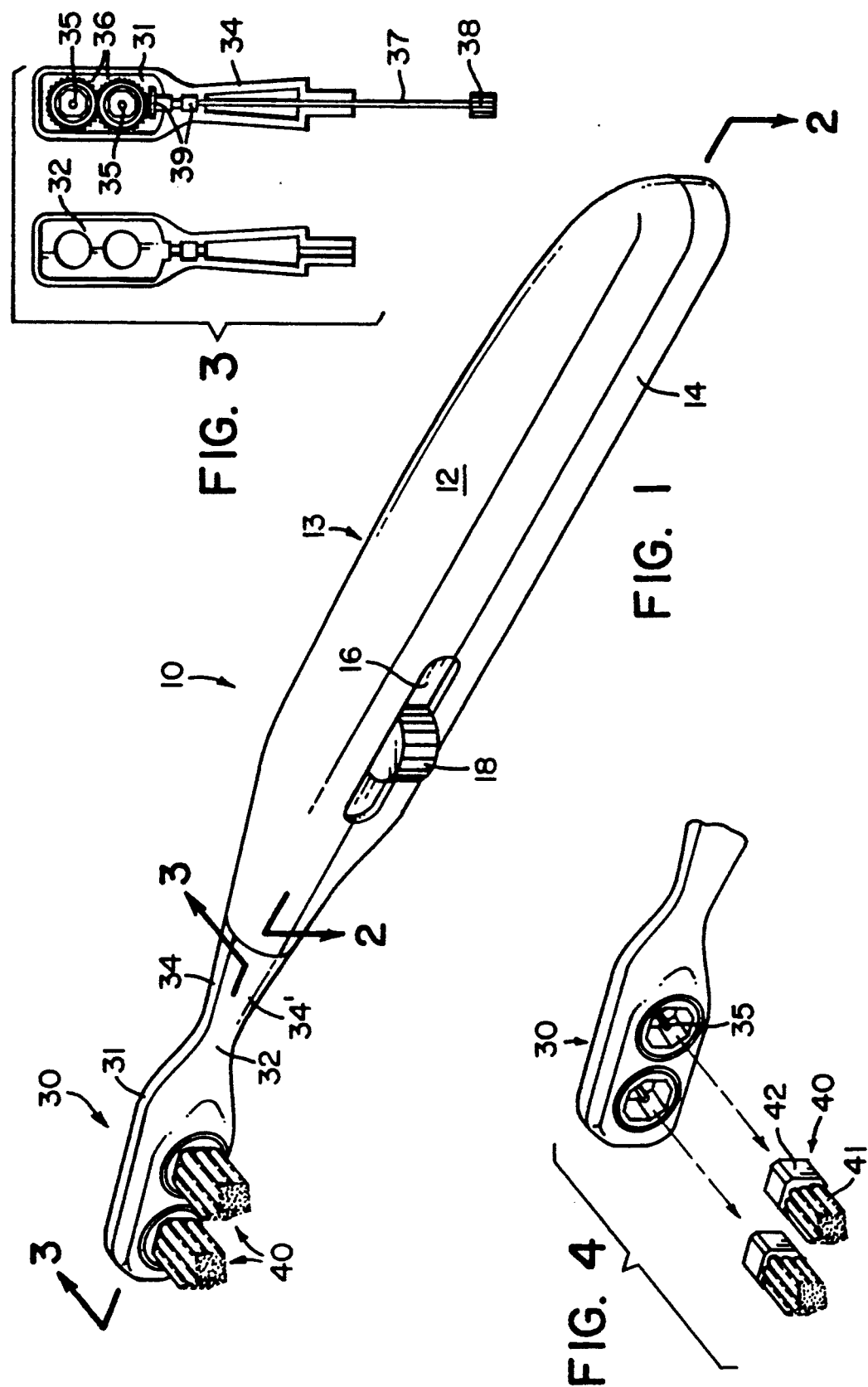

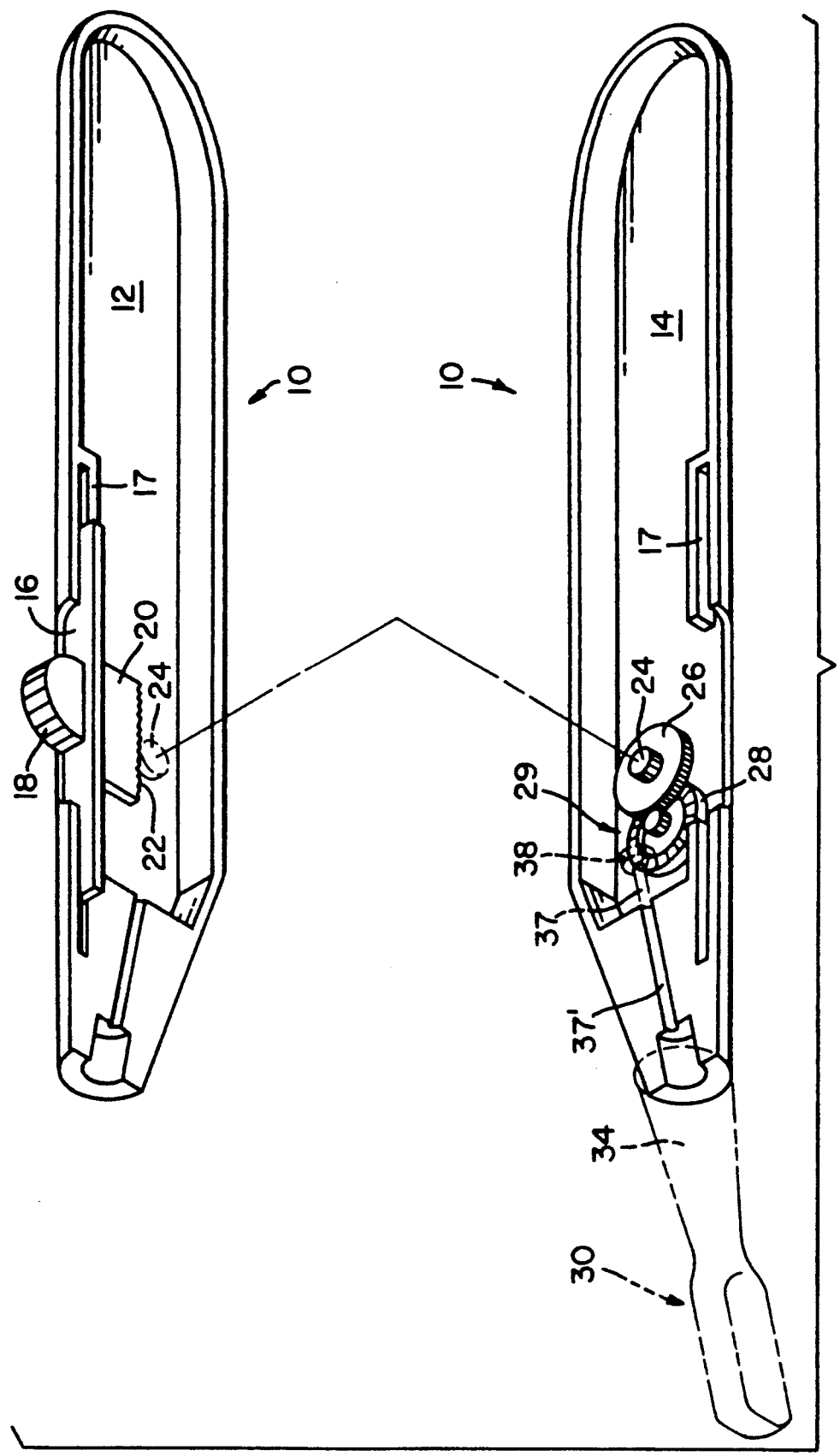

MANUALLY OPERATED ROTARY TOOTHBRUSH

BACKGROUND OF THE INVENTION

1. Field of the Invention

This invention relates generally to manually driven brushes and, specifically, to improvements in manually driven, rotary brush toothbrushes or similar apparatus.

2. Discussion of the Relevant Art

Over the past three decades, dental prophylaxis, in the form of regular brushing with decay-preventing dentifrices, has served to improve the nation's dental and general health to a significant degree. Notwithstanding the advances in dentifrices, there has been little improvement in the toothbrush used by the vast majority of persons practicing dental hygiene on a two- or three-time a day basis. That is not to say that changes in bristle quality, shape of the brush and/or size of the toothbrush article have not been improvements; but to the average toothbrush user, parametric changes to the conventional, straight handled "scrubbing" toothbrush comprise the preponderance of improvements to the original. Of course, there have been marketed numerous toothbrushes wherein the bristles or brushes of the apparatus move reciprocatively in lateral or longitudinal translation, and even those which possess rotary bristles or brushes. But, almost all of the truly successful products are motor driven. Short of returning to the pristine handbrush, there is a paucity of manually driven toothbrushes in which the bristles are caused to translate or rotate after the fashion of the many power driven brushes, as discussed above.

In making the instant invention, I performed a diligent search, not only on the market shelves and in catalogues, but in the records of the United States Patent and Trademark Office as well. Several patents were located, in the latter search effort, in which various patentees improved both power driven and manually operated toothbrushes in order to acquire certain characteristics and/or achieve specific goals. In the former category, power driven brushes, U.S. Pat. No. 4,079,517 issued to Zacharia discloses an electrically driven brush having an extension shaft from the end of which projects an orthogonally disposed rotary brush. Because the brush is electrically powered, Zacharia is particularly concerned with providing water tight seals in the power unit-extension shaft region and at the power unit-rotating shaft interface portion of the unit. A disadvantage of the '517 device is that, even were it not to require (as it does in this case) a transformer unit, the entire ensemble remains both bulky and relatively heavy; and it does not appear to be the type of device which one will readily carry to work and employ regularly away from the home or in the workplace. Although having the advantage of applying uniform force to the teeth and all areas of the mouth, the disadvantages, combined with the cost of production, make this device generally undesirable for usage away from the home. Only a manually operated (driven) and inexpensive device will overcome these disadvantages. In 1981, a power driven brush assembly was patented by Cohen, U.S. Pat. No. 4,274,173, and employed a triple rotary brush ensemble in the cleaning head. The triple rotary brushes are belt driven and therefore move unidirectionally. The main thrust of the '173 teaching appears to be in the cup-shaped cavities located in a free end of each individual brush. Further, the captured brush end appears to be removable from a rotary base which comprises a spur gear. The spur gear bases, however, are toothed in order to engage a drive belt and do not enmesh with each other. Further, a drive pin is used to fixedly secure the brush end in the spur gear base. In addition to having disadvantages which I have cited regarding the '517 device, the '173 employs a drive belt which, if broken, is not easily replaceable by the user. Further, although the patentee means to say that adjacent brush surfaces rotate in opposite directions, the brushes, nonetheless, rotate in the same direction. My studies have convinced me that there is no particular merit to this type of brush movement and, further, obtainment of such is usually at a cost of greater complexity than is either necessary or desired in the multiple brush ensemble. I prefer, as the reader will hereinafter see, to employ a plurality of contrarotating brushes because the scrubbing action is not diminished and the mechanization required for obtaining this function is less costly and far less contrived.

Final to my search of the patent records, a rotary toothbrush disclosed in U.S. Pat. No. 1,949,241, issued to Carlson et al., although encumbered by a thumb actuated rack and drive pinion design, is nonetheless noteworthy for its early genesis and unusual brush shape. Patent '241 employs a transversely mounted, thumb actuated, spring biased rack-on-plunger to engage a pinion gear compounded with a crown/spur gear. The crown gear (of the spur) engages a pinion mounted at the end of a drive shaft. At the other end of the drive shaft is a removably mounted helical brush. The thumb actuated, transversely mounted drive rack plunger has an inherently serious disadvantage. When the '241 brush is held in the hand and the thumb placed on the plunger and actuated to reciprocatively move the rack in a direction transverse the longitudinal axis of the brush, a force coexists which not only serves to rotate the helical brush but also causes a forcing of the brush head end away from the user's teeth. As the spring biased rack/plunger is rebiased, a natural tendency for the user would be to repress the brush onto the surface of the teeth. Thus, in the sporadic pumping action required to actuate the brush, the user inadvertently applies an irregular pressure, almost periodically, to the teeth. Because the thumb actuated rack is subject to a rebiasing mode, a strong deceleration is applied to the brush surface by contact with the teeth and the effects of the rebiasing mechanism then tend to be overridden. To correct this deficiency, a heavier rebiasing spring would only cause the user to apply more pressure to the thumb actuated rack-plunger and thus a greater force when "pushing" the brush off the teeth as (previously) mentioned. It would appear that in '241, actuation transverse the longitudinal axis of the brush is ill-advised in my judgement.

In order to provide a truly functional, portable and manually operable rotary brush device, improvements had to be directed toward certain disadvantages of the current art as well as those factors which encourage regular use of a mechanical contrivance in favor of the more conventional static toothbrushes of the genre.

SUMMARY OF THE INVENTION

I have invented a manually operated toothbrush which overcomes the disadvantages found in the earlier art. In order to avoid the most prominent disadvantage, an irregular or erratic force applied through the brushes to the surfaces of the teeth, I teach an apparatus that: (1) applies opposed brushing action at the gumline by use of contrarotating brushes; and (2) uniform pressure on the head of the toothbrush as the brushes are manually operated through the use of a thumb-actuated, longitudinally reciprocative slide mechanism. This slide mechanism allows application of a translational force alternatively toward and away from the head of the brush and coparallel with the longitudinal axis of the handle. I have determined, through my studies, that this is the best manual application of a (continuous) force that can be applied to the hand-held handle of the brush, while allowing the user to maintain maximum control of the brush head and apply a uniform "touch" to the surfaces of the teeth. Of course, contrarotation of the brushes assures that, as a user passes the head of the toothbrush over a row of teeth, a rotating bristle first will brush along the gumline in one direction and, as the head of the brush is directed to the adjacent tooth, an adjacent contrarotating brush will brush the first contacted tooth in the opposite direction (along the gumline).

I have set the elements which acquire the novel functions (above) mentioned into a light, relatively rigid and durable toothbrush container. The handle portion, as well as the head portion, are constructed of durable, light-weight and fairly rigid materials such as plastic, epoxy composite or metal. I employ an elongate, essentially hollow handle which has been molded, machined or otherwise formed from the aforesaid materials and have positioned therein and mounted for slidable action, a rack comprising a slide portion, a detent portion which projects outside the handle and upon which the user's thumb applies motivation, and an internal portion consisting of a (toothed) rack. Slidable mounting for the aforesaid is provided in the handle. Also provided is at least one compound spur gear consisting of a combination pinion and spur gear having either a bevel, conventional or crown arrangement of gears therewith. The rack portion of the slide mechanism engages the pinion which is compounded with the spur gear portion and causes it to rotate as the rack is translated to and fro over the pinion portion of the compound gear. This converts the longitudinally translating and reciprocating motion of the slide into a rotary motion as exhibited by an angular output from the spur portion of the compound gear. Thereafter, other spur gears may be used to form a gear train which ultimately ends in a spur gear having either a bevel gear on the perimetral edge thereof or a crown gear at a facial perimeter thereof. The reason for the bevel or crown type surfaces on the (single or) last spur gear of the driving gear train is to effect the transmission of rotary motion to a pinion gear which is fitted to a drive shaft that extends from out of the housing and shank portion of the head casing. Turning to the head portion of the toothbrush, a housing, which is the head proper, encases at least two spur gears which are enmeshed (and) of which one contacts a crown gear located at the other end of the aforesaid drive shaft. A goodly portion of the drive shaft is then passed through the shank portion of the head and extends into the brush handle where the other end of the drive shaft, bearing the aforesaid pinion gear, makes contact with the bevel or crown surface of the aforesaid (single or) last gear in the gear drive train of the mechanism. The housing and shank portions forming the integral head of the mechanism are fixed to the handle of the brush and may be readily removed therefrom, since the only coupling with the major portion of the drive mechanism is through the drive shaft extension which bears but a single pinion gear thereon. The entire mechanism is easily disassembled and discrete parts thereof replaceable.

The brush arrangement, because of the aforesaid spur gear base enmeshment, readily acquires contrarotation between adjacent brushes of the device. More particular to the spur gear bases, which are provided with sockets for the removable placement therein of brushes, are the brushes comprising one or more sets of bristles mounted in a bristle base which is geometrically fashioned to fit tightly into the spur gear (brush) base sockets. Thus, like every element of my invention, the brushes may be removed and replaced at the desire of the user.

BRIEF DESCRIPTION OF THE DRAWINGS

Of the drawings:

FIG. 1 is an isometric illustration of the invention disclosing the two major external portions;

FIG. 2 is a cut away double illustration of the FIG. 1 device taken at 2—2;

FIG. 3 is a plan view of the top and bottom portions of the head mechanism taken at 3—3 of FIG. 1; and FIG. 4 is an isometric illustration depicting the brushes of the device in relationship to the head mechanism.

DETAILED DESCRIPTION OF THE PREFERRED EMBODIMENT

As the following figures will now illustrate, I have embodied my improvements in this art in a very light, easy to handle mechanism that derives the motivational power for a pair of rotary brushes from a reciprocable, thumb-actuated mechanism that is encased in a handled brush which is held essentially in the palm and forefingers of the user's hand. The reciprocative thumb motion that is required to actuate the mechanism is a to-fro or push-pull action that is both natural and comfortable to individuals having reasonably full use of the thumb. It may be readily observed, by even the unskilled, that this type of motion practiced on an elongate handle such as I inculcate in the instant device, is readily controllable and is neither pushed away from nor pulled toward the user's mouth, as would be readily experienced by one attempting to effect a transverse-the-handle, plunging motion seen in the earlier-discussed art.

Referring more particularly now to FIG. 1, the isometric depiction herein of my preferred embodiment 10 consists in two halves 12,14 of an elongate, hollow handle 13, a brush head 30 and brush(es) 40; the latter two elements of which will be discussed more thoroughly hereinafter. Seen in the FIG. 1 illustration, relative to the handle 13, is a slide 16 enclosed principally within the handle 13 and secured between the right half 12 and the left half 14. Projecting outward of the handle, and affixed to the slide 16, is a detent 18 which consists in a rest for thumb force application by the user. The remaining principal portions of FIG. 1 consist in the toothbrush head 30, which is comprised of a base 31 and a cover 32, both of which extend to a shank 34 portion, and a pair of brushes 40. Reference to FIG. 2 shall apprise the reader of the internal mechanisms of the handle 13 and its mechanical interface with the head 30.

FIG. 2 is an isometric illustration of a partially exploded view of my preferred embodiment 10. The right half 12, the upper portion of the illustration displays the molded or cast form of the invention 10. Providable by ordinary skill of a manufacturer is a grooved receptacle 17 adapted for receiving therein the slide 16, which is of a length that will allow its (considerable) reciprocative motion as it lies in the groove 17. Rigidly affixed, or integrally formed with the slide 16 is the rack 20 which is a flange mechanism of essentially rectangular shape. It is longitudinally aligned with the slide 16, and further bears thereon, inward of the handle 13, a series of teeth or gear-like serrations 22. As the slide 16 is motivated in the groove 17, the teeth 22 of the rack 20 engage and rotate pinion 24 portion (in phantom) of compound pinion/spur gear 24/26. The latter mechanism is clearly illustrated in the lower section of FIG. 2 which relates to the mechanism internal of the left half 14 of the handle 13. As reference to this illustration half will illustrate, I have chosen to place an additional gear in the gear train which serves to transfer the reciprocative thumb motion of the user to the brush drive shaft 37 (in phantom). This double gear transmission is not always necessary; those of ordinary skill will recognize that, in lieu of the additional compound spur-bevel/crown gear 28, the crown gear 29 of gear 28 could be readily placed on spur gear 26, either as a crown or bevel mechanism in order to drive pinion 38 (in phantom) which is rigidly affixed to the end of drive shaft 37. Drive shaft 37 is, of course, allowed to rotate freely in channel 37' in order to extend on into the shank 34 portion of the head 30. Once the rotational force is delivered to drive shaft 37, the angular motion thereof is transferred to the head 30 and the mechanism contained therein.

As will be clearly illustrated in FIG. 3 (a plan view depicting the major mechanisms lying within the back portion 31 of the head 30, shank 34 (right side of figure) and the cover 32), the brush drive mechanism is elegant in its simplicity and of high utility in its discrete part functionality and replaceability. The head portions 31,32, with coextensive shafts 34, 34', are carefully formed so as to allow the brush drive mechanism to reside within the illustrated encasement, move freely therein and be readily removed once the head 30 halves 31,32 are separated. I have not digressed herein to discuss matters such as joining of the handle halves 12,14 or the head portions 31,32. It may be accomplished by using detent-in-receptacle portions along the perimetral edges of the parts, small screws or clips or, if repairability is not desired, adhesive bonding or chemical welding. Such is left to the choice of the manufacturer. As to the identification of the mechanisms in the head 30 and shank 34, the reader's attention is called to the right hand illustration of FIG. 3. Positioned in the shank 34 is the drive shaft 37 bearing pinion gear 38 at the in-handle section of the invention 10, and at the other end thereof a crown gear 39. Mounted in tandem are two spur gears 36 possessing sockets 35 therein which have a generally rectangular shape. Once again, those of ordinary skill will readily recognize that the only geometric shape required in the sockets 35 of the spur gear bases 36 is one that will not allow free rotation of the brushes 40 therein. Since it is my intention to make at least the brushes replaceable, I have selected a tight fitting, non-rotational geometry as the shape of the sockets 35 in spur gear bases 36 which are to be used for receiving therein the bristle bases 42 (not shown) of the brushes 40 (not shown). Once the cover 32 is placed over the back portion 31 of head 30, the well-like apparatus for receiving the brushes therein will be readily seen, as illustrated in FIG. 4. Before leaving the discussion of FIG. 3, the reader's attention is called to the spur gear base 36 enmeshment and the enmeshment of one spur gear base with crown gear 39. Routineers in this art will recognize that this simple alignment assures that adjacent gears will contrarotate during operation.

Referring finally to FIG. 4, the assembled head portion is displayed in isometric illustration with brushes 40 poised for insertion into brush sockets 35 so as to be seated firmly in the spur gear bases 36. The brushes consist in bristles 41, permanently affixed to bristle bases 42. The bristle bases are made of durable materials so that the bristles 41 will be held in the desired position as determined by the brush designer. I prefer to use a bristle base for the brushes that will be snugly insertable into the spur gear base 36 sockets 35, yet remain removable simply by the user grasping the bristles in one hand, the head 30 in the other, and tugging smartly in the directions illustrated in FIG. 4.

Users of my invention will readily recognize the benefits of its use as a tool for daily dental prophylaxis. The unique, thumb actuated drive mechanism, which is operated by a comfortable application of a natural thumb maneuver, coupled with the contrarotating brush ensemble, is of inestimable value when one considers its utility, affordability and ready portability. This invention is commended to others in the field who may make other modifications to it consistent with the spirit and scope of the hereinafter appended claims.

What is claimed is:

1. A hand-held rotary toothbrush comprising:
    a hollow, elongated handle containing therein an elongated, recessed groove extending longitudinally along said handle, said groove slidably supporting a sliding mechanism therein, said sliding mechanism including an elongated flat slide extending longitudinally along said handle and received in said groove, a detect which projects from said slide outwardly from the handle for receiving a user's thumb thereon and a rack gear which extends from said slide inwardly inside the handle, said sliding mechanism being adapted to move along said recessed groove in response to a straight, reciprocative actuation force applied to said detect by said holder's thumb;
    a head, operatively secured proximate an end of said handle, said head rotatably housing at least two adjacent gear bases therein, said bases being in rotatable gear contact with one another, each gear base supports a brush element extending from said head;
    an elongated rotary shaft having a rotary gear at one end for transferring a rotary motion thereof to one of said gear bases, said one of said gear bases being in meshing gear contact with said rotary gear of said rotatable shaft; and
    gear means disposed within said handle and operatively coupled to said rack gear for converting the movement of said sliding mechanism along said recessed groove, due to the straight, reciprocative actuation force applied to said detent by said holder's thumb, to a rotary motion and for applying said rotary motion to said rotatable shaft.

2. The toothbrush of claim 1 wherein the head further comprises an elongated housing having a major axis which is collinear with the handle, the housing containing said gear bases, each said gear base having a spur gear which rotatably contacts at least one other spur gear of an adjacent base, the head having a hollow shank which connects it to the handle and wherein the shank includes a longitudinal conduit therethrough for receiving said rotatable shaft therein, said rotatable shaft having a first end portion engaging one of said spur gears and an opposing end portion receiving said applied rotary motion.

3. The toothbrush of claim 2 wherein said first end portion of said rotatable shaft includes said rotary gear which is formed as a crown gear and wherein the opposing said end portion of said rotatable shaft includes a pinion gear.

4. The toothbrush of claim 1 wherein said gear means includes at least one compound spur gear for engagement with said rack for converting the reciprocative movement of said sliding mechanism to a rotational motion.

5. The toothbrush of claim 1 wherein the brush elements supported by said gear bases comprise removable brush elements.

6. The toothbrush of claim 1 wherein said gear bases comprise spur gears, each said gear base having therein a socket receptive of a push-on, pull-out brush element.

7. The toothbrush of claim 1 wherein said gear means includes at least one compound gear having a pinion gear which is concentrically and rigidly fixed to a face of a second gear.

* * * * *